United States Patent [19]
Fischer

[11] Patent Number: 5,770,855
[45] Date of Patent: Jun. 23, 1998

[54] MICROSCOPIC ELECTROMAGNETIC RADIATION TRANSMITTER OR DETECTOR

[76] Inventor: Ulrich Fischer, Althausweg 103, D-48159 Münster, Germany

[21] Appl. No.: 640,942
[22] PCT Filed: Sep. 5, 1995
[86] PCT No.: PCT/EP95/03491
  § 371 Date: May 7, 1996
  § 102(e) Date: May 7, 1996
[87] PCT Pub. No.: WO96/07946
  PCT Pub. Date: Mar. 14, 1996

[30] Foreign Application Priority Data

Sep. 9, 1994 [DE] Germany .......................... 94 14 582 U

[51] Int. Cl.⁶ ..................................................... H01J 3/14
[52] U.S. Cl. ........................................... 250/216; 250/306
[58] Field of Search ..................................... 250/234, 306, 250/307–311

[56] References Cited

U.S. PATENT DOCUMENTS

| | | | |
|---|---|---|---|
| 4,604,520 | 8/1986 | Pohl ........................................ | 250/216 |
| 5,270,543 | 12/1993 | Visser et al. ............................ | 250/306 |
| 5,289,004 | 2/1994 | Okada et al. ........................... | 250/306 |
| 5,389,779 | 2/1995 | Betzig et al. ........................... | 250/306 |

FOREIGN PATENT DOCUMENTS

| | | |
|---|---|---|
| 0 112 401 | 7/1984 | European Pat. Off. . |
| 459392 A2 | 12/1991 | European Pat. Off. . |
| 487233 A2 | 5/1992 | European Pat. Off. . |
| 43 29 985 | 5/1994 | Germany . |

OTHER PUBLICATIONS

Science, vol. 251, pp. 1468–1470 — E. Betzig, J.K. Trautman, T.D. Harris, J.S. Weiner, R.L. Kostelak [1991] "Breaking the Diffraction Barrier . . . ", Jan. 1991.
Appl.Phys. Lett. 44, 651–653, D.W. Pohl, W. Denk, M. Lanz [Jan—1984] "Optical stethoscopy: Image recording with . . . ".

Primary Examiner—Que Le
Attorney, Agent, or Firm—Collard & Roe, P.C.

[57] ABSTRACT

The present invention relates to a microscopic electromagnetic radiation transmitter or detector and a so-called near-field probe (1) whose body takes the form of a polyhedron point and consists of a material which is at least partially permeable to electromagnetic radiation in the spectral region used. The polyhedron point is delimited by an imaginary base surface beyond which the substantial part of the body is continued to form a total probe body, which is not defined in greater detail. The polyhedron point has "n" side faces and edges leading to an acute point (2) are formed between adjacent side faces. According to the invention, at least two side faces of the body of the polyhedron probe (1) are coated with thin, electrically conductive layers which absorb some of the electromagnetic radiation in the spectral region used, preferably consist of materials such as aluminum, gold or silver and are less than 0.2 μm thick. The front part of the polyhedron point (2) is also coated with the material used, resulting in an efficient near field probe with comparatively high resolution in optical near field scanning microscopy, simultaneous scanning tunnel microscopy also being possible with the same point.

9 Claims, 8 Drawing Sheets

MICROSCOPIC ELECTROMAGNETIC RADIATION TRANSMITTER OR DETECTOR

BACKGROUND OF THE INVENTION

1. Field of the Invention

The present invention relates to a microscopic transmitter or detector of electromagnetic radiation which, hereinafter, is referred to as a near-field probe (1), the body of which has the form of a polyhedron point and consists of a material that is at least partially permeable to electromagnetic radiation in the spectral range used, whereby the polyhedron point is delimited by an imaginary base surface beyond which the substantial part of the body is continued to form a total body of the probe not defined in greater detail, said polyhydron point having "n" side faces in a way such that sharp edges are formed between adjacent side surfaces, such edges leading to an acute point, whereby the point of the near-field probe serves as an almost point-like source for emitting electromagnetic radiation into the external space of the probe, or as an almost point-like receiver for the penetration of electromagnetic fields into the interior of the near-field probe, whereby at least two side surfaces of the body of the polyhedron probe are coated with thin, electrically conductive layers, the latter partially absorbing the electromagnetic radiation in the spectral range used, and preferably consisting of material such as aluminum, gold or silver and having a thickness of less than 0.2 $\mu$m.

2. The Prior Art

Known probes of the above type have the property that is important to their sensor function, which is that an aperture is mounted on the point in a metal film. Said known probes include:

(a) the probes of Pohl (D. W. Pohl, W. Denk, M. Lanz [1984] Appl. Phys. Lett. 44, 651-653), consisting of a glass or quartz fiber ending in a point, such fiber being coated with metal in such a way that an aperture is available on the point in the metal coating.

(b) The probe of Betzig et al (E. Betzig, J. K. Trautman, T. D. Harris, J. S. Weiner, R. L. Kostelak [1991]; Science Vol. 251, 1468-1470), which, in a way very similar to the one of Pohl et al, consists of glass fiber coated with metal and ending in a point, the metal coating of said fiber having a submicroscopic aperture on the point. Because of the aperture in the metal coating, the front part of the point is uncoated. Said probes have the drawback that the complex structure of an aperture in a metal film directly on the point limits the minimum dimensions of the point to about 0.1 $\mu$m, whereby the aperture must not be smaller than about 15 nm. Therefore, it has to be expected that with the resolution of 13 nm achieved, the limit of the resolving capacity of the scanning near field optical microscopy SNOM (Scanning Near Field Optical Microscopy) has been reached with such points. At the same time, the width of the point of at least 0.1 $\mu$m conditions that the aperture can be brought close to the surface to a distance of less than 15 nm only in exceptional cases, such distance being required for obtaining the resolution of 15 nm.

The tetrahedron probe described by Danzebrink and Fischer, which is specified in application DE 43 29 985 A1, has the same drawback. However, versus the probes described above in (a) and (b), said probe has the advantage that it satisfies the function of the transmission element in a superior way.

Since the aperture satisfies the function of the SNOM-probe in both cases, said probe not being electrically conductive everywhere, a simultaneous SNOM and scanning tunnelling microscopy with high lateral resolution is not possible with the identical point in said cases.

SUMMARY OF THE INVENTION

The invention is based on the problem of creating an efficient near-field probe with which a resolution as high as possible can be achieved in scanning near-field optical microscopy, and which permits simultaneous scanning tunnelling microscopy with the same point.

The solution of said problem is obtained according to the invention in that also the most frontal part of the polyhedron point is coated with the coating material used. Said device has the advantage that the resolution of a near-field microscope equipped with said probe is no longer limited by the aperture because the most frontal part of the point itself serves as the emitter or receiver of electromagnetic fields. Furthermore, since the most frontal part of the point is coated with an electrically conductive material, the near-field probe can be used both in optical near-field microscopy with high resolution and at the same time also in scanning tunnelling microscopy.

The developments of the idea of the invention described in the dependent claims contain additional advantages.

Further benefits and features of the invention become clear from the following specification of a number of preferred exemplified embodiments with reference to the attached illustrations, in which:

DETAILED DESCRIPTION OF PREFERRED EMBODIMENTS

Figures 2A, 2B:
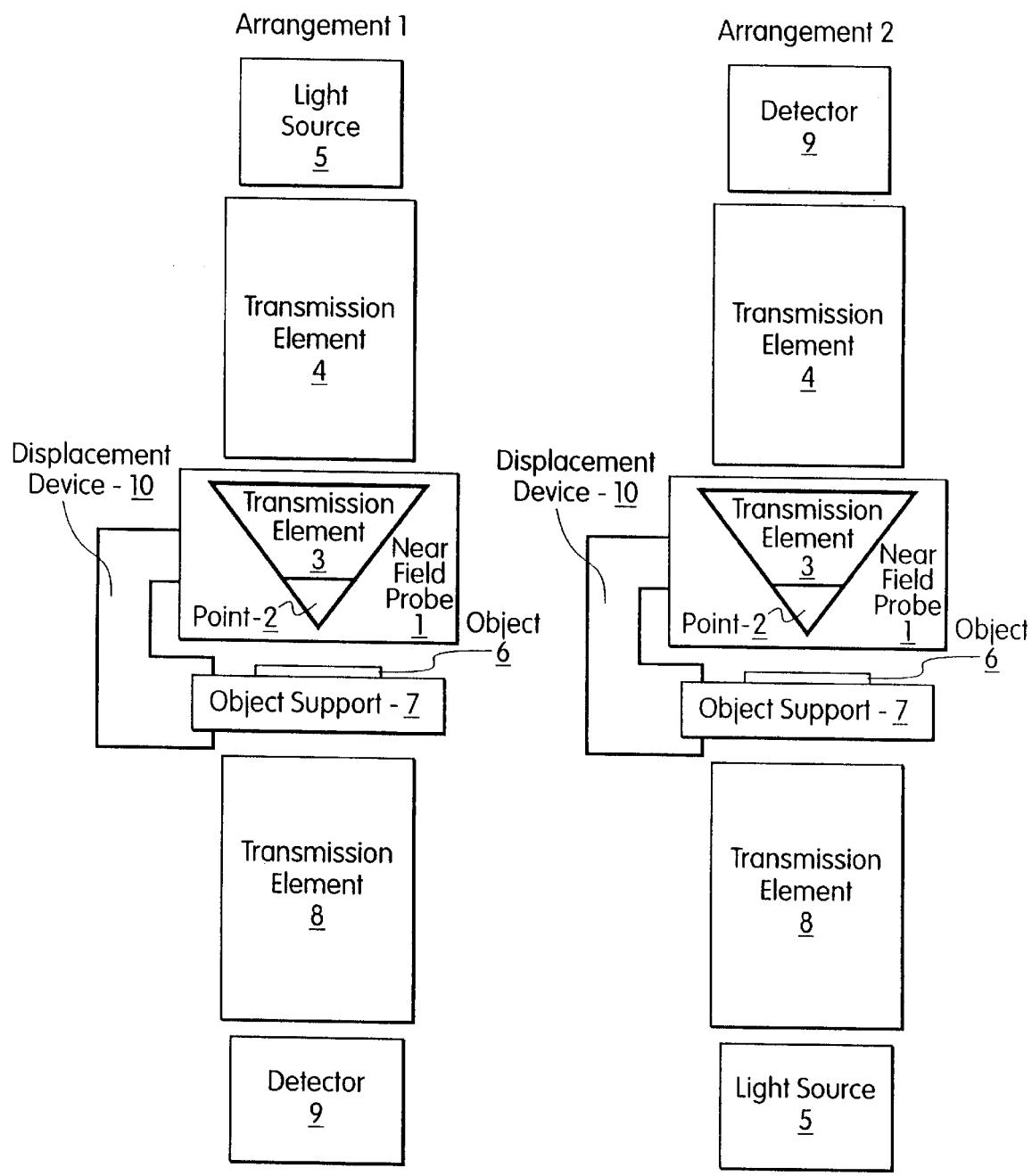
FIGS. 2A and 2B show a schematic representation of the arrangements of the polyhedron probe in an optical near-field microscope.

In connection with known arrangements of scanning near-field optical microscopy SNOM (Scanning Near-Field Optical Microscopy), a point 2 with submicroscopic dimensions that are smaller than the wavelength of the electromagnetic radiation used, in the arrangement I (FIG. 2A) serves as a submicroscopic transmission antenna, and in the arrangement II as a receiving antenna. In the arrangement I, light emitted from a light source 5 is transmitted onto the near field probe 1 via a transmission element 4. The transmission member 4 may be a wave conductor such as, for example a glass fiber, or an optical radiation path with lenses, or also a combination of a number of such components. An additional transmission element 3 serves for transmitting light energy from the transmission element 4 to the point 2. The transmission element 3 also serves the purpose of transmitting to the point 2 light from a region with dimensions that are large versus or comparable to the wavelength of the light, such a point having dimensions that are small as compared to the wavelength. The transmission element 3 and the point 2 are the essential components characteristic of the design of a near-field microscope. Said components form the near-field probe 1. The point 2 is mounted within the direct proximity of the surface of the object 6, which is supported by an object support 7. A displacement device 10 serves the purpose of displacing the object in three dimensions relative to the point. Light reflected by the object 6 is transmitted by a transmission element 8 to the detector 9, which serves the purpose of converting the signal received into an electrical signal, which is the near field signal, which is processed further as the signal for the optical near-field microscopy. In the arrangement II (FIG. 2B) with the point 2 serving as the receiving antenna, the positions of the source 5 and the detector 9 are exchanged. If the source 5 and the detector 9 and the associated paths of energy transmission to the point 2 or the object 6 are arranged on opposite sides of the object 6 as shown in FIG. 2, such an arrangement is called a transmission arrangement. If said components are mounted on the same side of the object, such an arrangement is called a reflection arrangement. In optical near-field microscopy, use is made of the fact that the object 6 has a retroactive effect on the emission or absorption of the probe 1 within the immediate proximity of the point 2, i.e., within the range of the near field of the probe, so that the signal (optical near field signal) received by the detector 9 is a characteristic function of the spacing between the point 2 and the surface of the object, and also of the local optical properties of the surface of object 6. The point 2 is guided across the surface of the object 6 with a spacing ranging from half of the wavelength to less than one nm. The optical near-field microscopy was demonstrated in a number of different versions, which substantially differ from each other on account of the type of probes 1 used and the arrangements of the probes for the microscopic procedure, i.e., on account of the type and arrangement of the transmission elements 3, 4 and 8 for the routes of energy transmission between the point 2 and the detector 9, on the one hand, and between the source 5 and the point 2 on the other hand.

Figure 1:
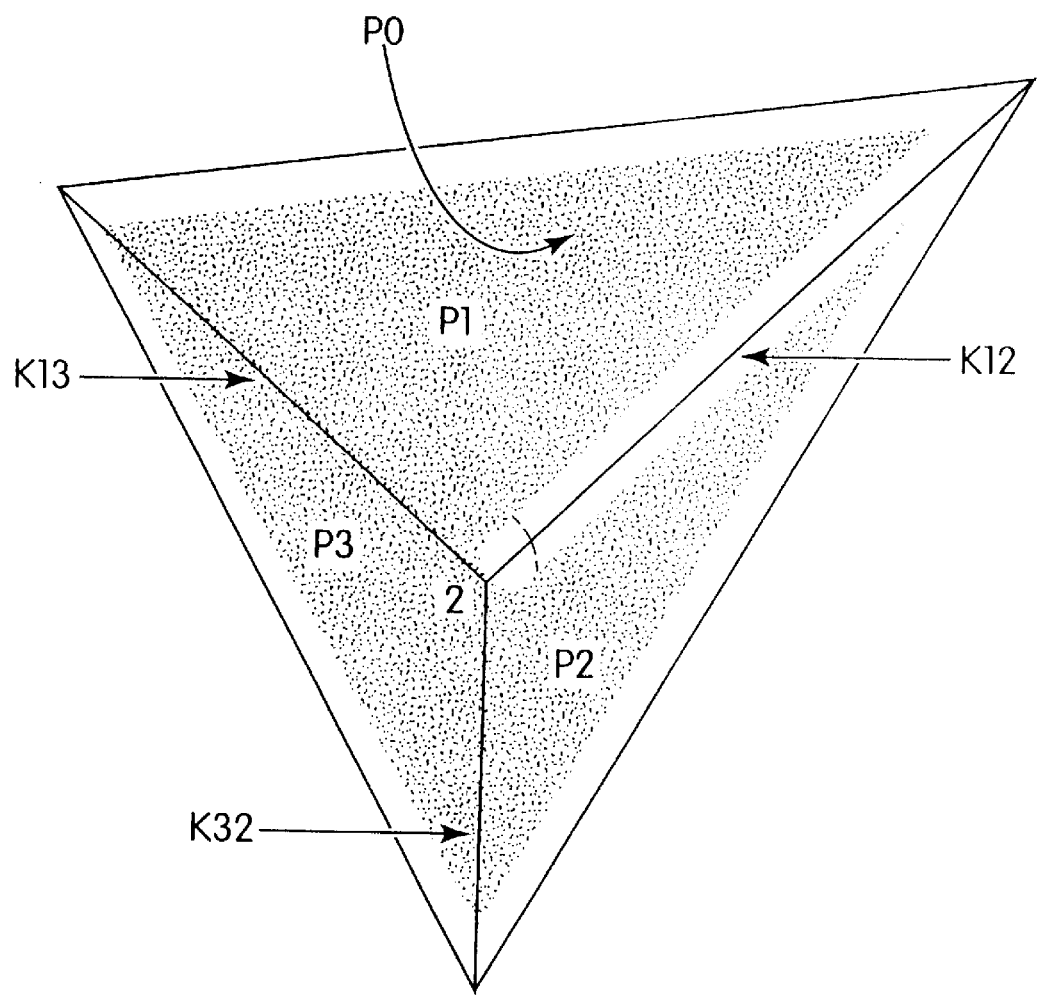
FIG. 1 shows a schematic representation of the polyhedron probe.

A probe according to the invention may have the shape shown in FIG. 1 for the case of the tetrahedron point (n=3), which is a polyhedron leading to a point 2 and made of a transparent material. The side surfaces $P_j$ (j=1, . . . , n) are coated with thin films of an electrically conductive material partially absorbing the electromagnetic radiation such as, for example, an electrically conductive metal, in a way such that the part of point 2 projecting farthest consists of the coating material. The edges $K_{ik}$ between the coated surfaces $P_i$ and $P_k$ may be uncoated or coated with the coating material as well. Uncoated edges may serve the function of transmitting electromagnetic energy from macroscopic dimensions into the microscopic range of the point 2, as described already earlier in laid-open specification (DE 43 29 985 A1). They have the function of the transmission element 3 in FIG. 2. Furthermore, it is possible to coat only two of the side surfaces $P_j$ (j=1, . . . , n) and the part of point 2 projecting farthest, whereby the edge $K_{ik}$ between the two coated side surfaces $P_j$ (j=1, . . . , n) may be coated or uncoated.

The design of the base surface $P_o$ remote from the point is left open, said surface may be, for example a ground surface, but it also may be an imaginary separation surface for continuing the polyhedron to form a suitable body of any desired dimension.

The transparent material of the body of the near-field probe may be a transparent amorphous glass, but also transparent crystalline material such as diamond, quartz, saphire, or also silicone for the infrared spectral range. Also, it may be material with higher nonlinear susceptibilities such as, for example lithium niobate, or photoluminescent material such as, for example doped glasses or crystals. The material must not necessarily be homogeneous and isotropic. The surface of the body or cutouts of the surfaces of the body may be provided with a thin layer of another refractive index, with a contamination layer, a doping layer, or with a thin coating consisting of another material.

The body K of such near-field probes can be manufactured in all sorts of different ways. A few manufacturing processes are described in the following. If amorphous or polycrystalline materials such as, for example glass are used, fractions can be produced in different directions. By fracturing a glass body several times it is possible, for example to produce a tetrahedron point. Said method of fracturing for producing the body of polyhedron probes is applicable to other materials as well, in particular also to crystalline materials, in which fractures are preferably produced along selected crystal planes. By controlled slight cutting and splitting along said planes it is possible to produce very exact edges and, if need be, corners.

Furthermore, it is possible to produce such edges and surfaces by grinding, polishing and etching methods as well.

Furthermore, it is possible to produce such points by microlithographic methods, as it is known, for example in the case of silicone points, which are transparent in the infrared spectral range.

Figure 3:
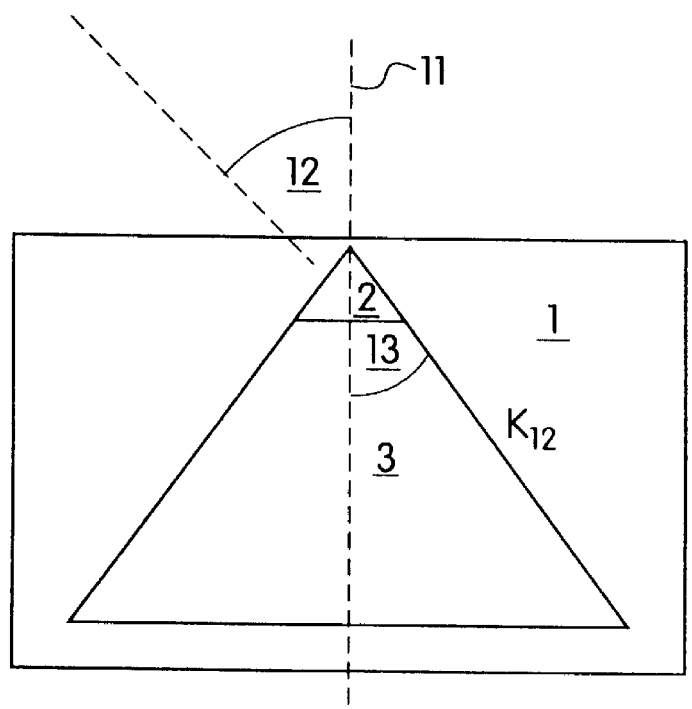
FIG. 3 shows a schematic representation relating to the coating of the polyhedron probe by rotation evaporation coating.

The side surfaces $P_j$ (j=1, . . . , n) may be coated with a thin film of a coating material, which may be applied by sputtering or thermal evaporation, or also by other methods. Coating may be carried out, for example by rotation vapor deposition, in which process the polyhedron point rotates during vapor deposition around the axis 11 extending through the point. Said rotary axis 11 is inclined relative to the vapor jet by an angle 12 smaller than 90°, as shown in FIG. 3, whereby the angle 12 may be varied during the coating process. On this way, the point and all side surfaces and all edges between the side surfaces are coated with metal.

Figure 4:
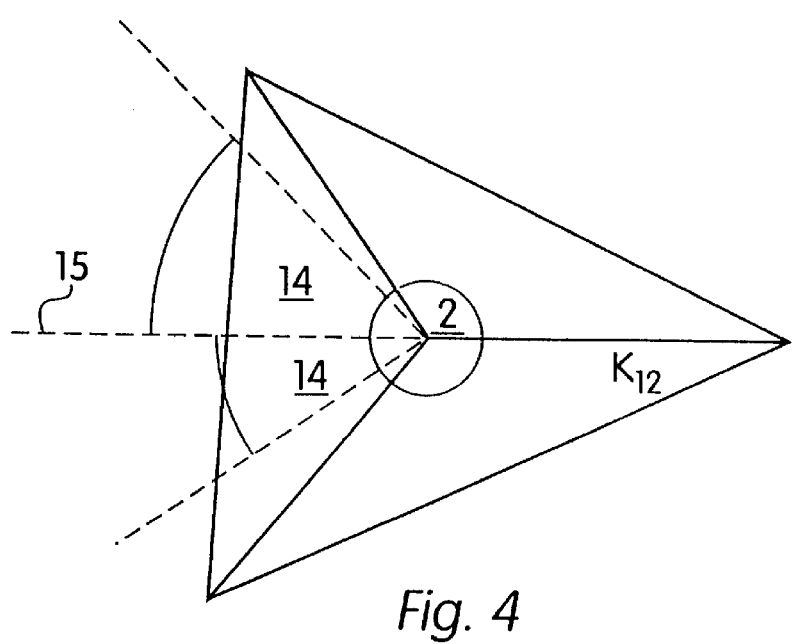
FIG. 4 shows a schematic representation relating to the coating of the polyhedron probe with an uncoated edge.

On the other hand, for the case of the tetrahedron point, the coating of two adjacent side surfaces $P_1$ and $P_2$ can be carried out in two steps, in a way such that the edge $K_{12}$ remains uncoated or is coated with a layer thickness that is thinner as compared to the coating of the side surfaces. The sides are coated successively with a material vapor jet the direction of which is inclined with an angle 12 smaller than 90° relative to the axis 11 extending through the point, whereby the angle 12 is, at the same time, greater than the angle 13 between the edge $K_{12}$ and the axis 11, and its direction is, furthermore, inclined at an angle 14 smaller than 90° relative to the axis 15 extending through the edge $K_{12}$ (FIG. 4).

Also in case of a polyhedron point with any desired number of side surfaces it is possible to carry out the coating process in such a way that one edge is uncoated whereas all sides, all other edges and the point are coated. In this case, coating takes place within the ranges of angles (12) and (14) specified above, whereby said angles may be varied in the course of the coating process.

In preferred embodiments of the invented polyhedron probe 1, the sharp edges $K_{ik}$ leading to a point, the coatings with the coating material and the material of the probe satisfy functions that are of significant importance to the property of such a probe as a submicroscopic transmitter or receiver of light.

Preferred embodiments of the probe and its mode of operation are described in greater detail in the following.

(1) The body of the polyhedron point 1 consists of a material which is transparent for the spectral range of the electromagnetic radiation used. The material of the tetrahedron is a transparent dielectric such as, for example glass, quartz, saphire or diamond. The coating of all sides $P_i$ consists of a thin metal layer such as, for example aluminum, gold or silver, whereby the edge $K_{12}$ between the two sides $P_1$ and $P_2$ is uncoated and the point 2 is coated.

The coatings and the uncoated polyhedron edge $K_{12}$ between the coated side surfaces serve the function of the wave conductor structures 3, with the help of which electromagnetic energy can be efficiently transmitted along the edge to the point 2. An analogy exists between the uncoated edge and the known double-wire wave conductor, which permits the transmission of electromagnetic energy along a cross section that is small as compared to the wavelength. The wave conduction is interrupted by the metallic point 2, from which the electromagnetic energy is reflected.

(2) Polyhedron point 1 made of transparent material, in connection with which all sides $P_i$ (i=1, . . . , n) and the point 2 are coated with metal. The semitransparent metal layers and the edges serve for transmitting electromagnetic energy in the form of surface waves. The wave conduction is interrupted by the point, from which the electromagnetic energy is reflected. Surface waves in the form of surface plasmonae can be produced on a metal coating by irradiation from the inside of the probe 1. With suitable selection of the angle of incidence of the radiation, exitation of the surface waves takes place relative to the surface $P_i$. In the edges, the conditions of generating surface waves are different from those on the side surfaces due to the changed geometry. For this reason, with suitable selection of the angles of incidence of the irradiation light, the preferred wave conduction can be obtained along the edge structure.

(3) The body of the polyhedron probe 1 consists of photolumineacencing material, or of a material which, in the regions of the surface enclosing the point 2, is doped with photoluminescent centers. The photoluminescence is stimulated as the light is being transmitted into the photolumineacent regions. Because of the wave conductor property of the edge, the spectrally shifted fluorescence light is transmitted along one edge to the point 2, from where it is reflected.

(4) The same arrangement as the one in (3) is used in order to produce a stimulated emission of the luminescenging centers in the polyhedron point at higher irradiation intensities. When selecting known suitable luminescence centers, the stimulated emission leads to laser activity, which can be detected based on a nonlinear increase in the radiation emitted by the point with increasing irradiation intensity.

(5) This embodiment is different from the embodiment 2 or 3 on account of the fact that the body of the polyhedron probe consists of nonlinear optical material with high nonlinear optical susceptibilities such as, for example, lithium niobate. At high irradiation intensities, irradiation of the polyhedron point with low-frequency light leads to doubling of the frequency or to frequency division and emission of said light from the point, such light being frequency-shifted versus the irradiation light.

The polyhedron points can be used in many different ways as near-field probes for optical near-field microscopy.

(1) With some transmission arrangements, the polyhedron point has the function of a submicroscopic transmitter (arrangement I). Stimulation of the probe for radiation takes place through irradiation via the transmission elements 4 and 3, and light emitted by the point 2 is used as the signal for the near-field microscopy.

(2) With other transmission arrangements, the point 2 of the probe 1 has the function of a submicroscopic receiver for light (arrangement II). Exciting of the probe takes place through light, which is emitted from the object 6. The energy transmitted from the point 2 via the transmission elements 3 and 4 serves as the optical near-field signal.

Figure 5:
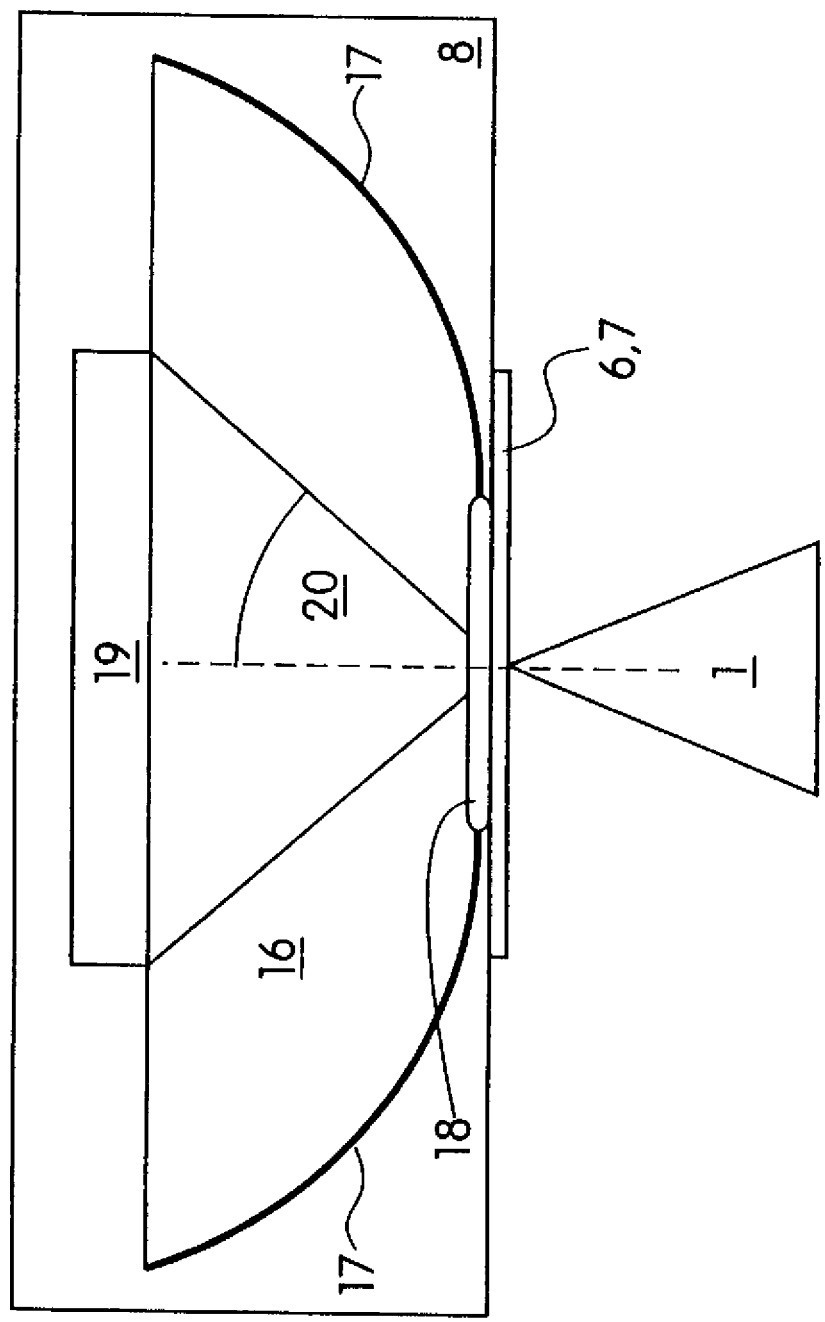
FIG. 5 shows an inverse dark-field collector for inverse photon tunnelling microscopy.
Figure 6:
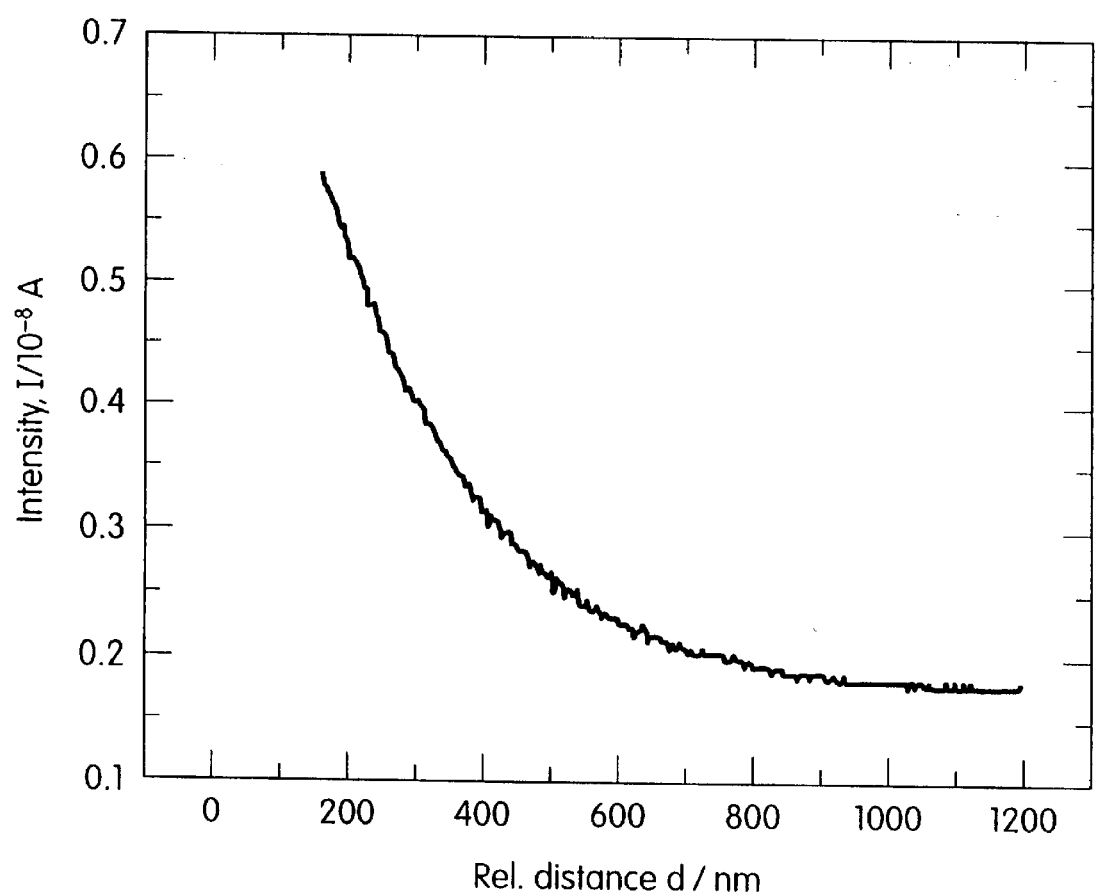
FIG. 6 shows a measured dependence of the near-field signal on the spacing in an inverse photon tunnel microscope; the intensity of the near-field signal is plotted on the ordinate and the relative spacing between the point (2) and the object (6) is plotted on the abscissa; the absolute spacing is not known.
Figure 7:
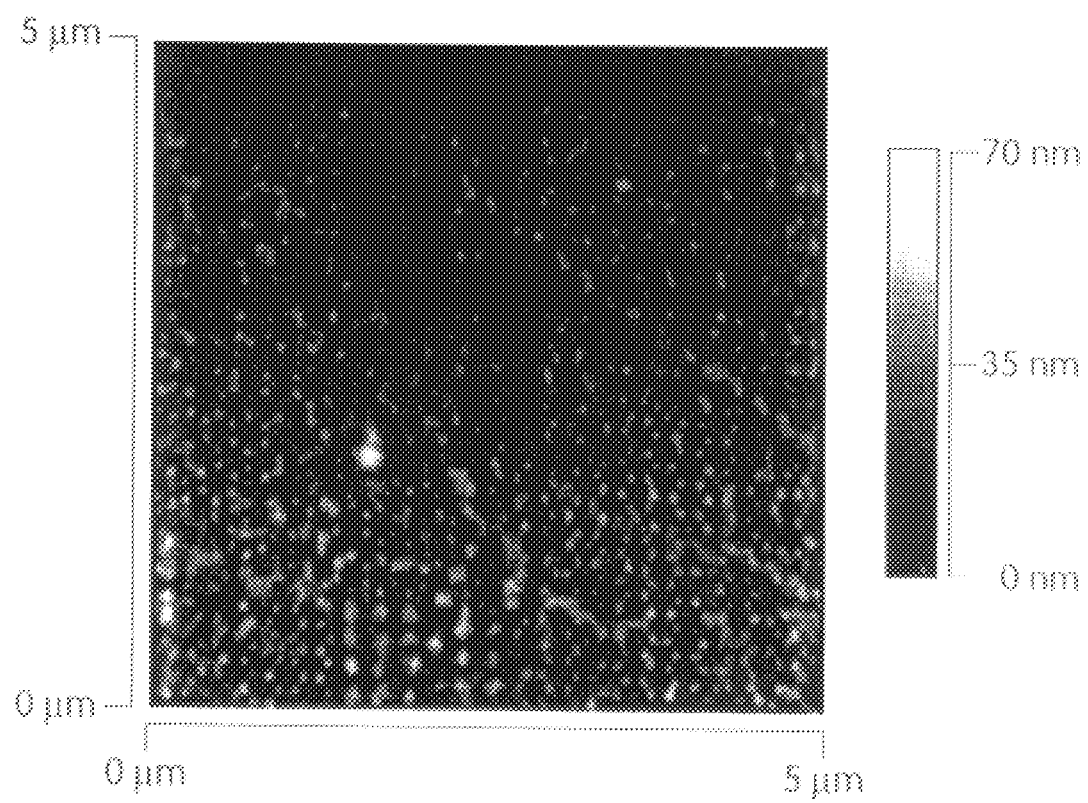
FIG. 7 shows a scanning force-microscopic image of the test object.
Figure 8:
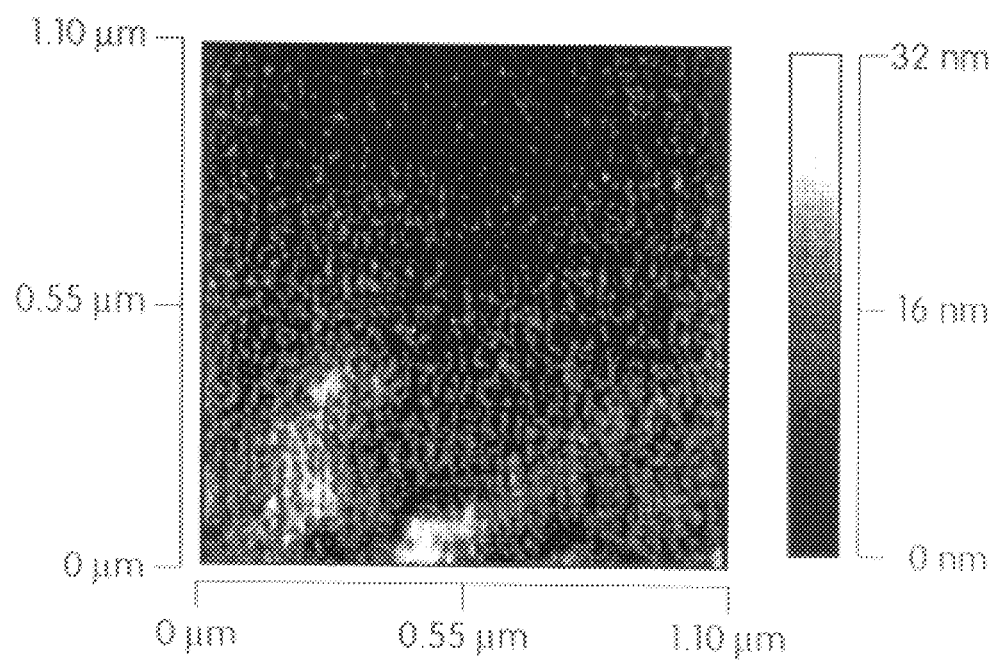
FIG. 8 shows an image of the test object with an inverse photon tunnelling microscope with a tetrahedron point having the design 1.

(3) In a specially realized arrangement of the near-field probe in an inverse photon tunnelling microscope (FIG. 5), the near-field-probe I serves as the transmitter as described for arrangement I. The object 6 is adsorbed on a thin, commercially available cover glass serving as the support 7. The cover glass is mounted on a dark-field immersion collector with the help of the immersion oil 18. Said collector forms a component of the transmission element 8 in arrangement I. The collector consists of a dielectric body 16, which has the form of the segment of a rotation paraboloid. Said paraboloid is provided on the side with a reflecting layer 17. The uncoated side surface may alternatively serve as the reflecting surface as well. The tetrahedron point 2 is arranged within the focal zone of the parabolic mirror. A circular opaque beam stop 19 is mounted on the outlet surface of the parabolic mirror. Said beam stop covers the part of the light transmitted through the collector that is reflected from the focal point of the parabolic mirror into the cone, which is limited by the limit angle of the total reflection 20. An immersion lens can be used instead of the parabolic mirror as well. The light transmitted by the collector is received on the detector 9. Said arrangement with the dark-field immersion collector serves the purpose that light emitted by the point 2 is received on the detector 9 only if the tetrahedron point is brought close to the object within the range of the evanescent modes of the air/glass interface of the cover glass. In this way, a signal is obtained that grows exponentially with the decrease in the spacing of the tetrahedron point from the cover glass, as shown in FIG. 6. Said signal serves the purpose of adjusting the spacing between the point and the cover glass with the help of an electronic controller and the adjusting element 10, in a way such that a preset should-be value of the signal is always maintained. For recording a screen picture, the cover glass is displaced raster-like relative to the tetrahedron point 1 with the help of the adjusting element 10. The trailing of the point in the axial direction, such trailing being conditioned by the controller, is recorded as the signal for producing the picture. In this way, pictures of a test object were recorded with the tetrahedron point of design 1. FIG. 7 shows a picture of the test object, which was recorded with a force microscope. FIG. 8 shows the near-field optical recording of the cutout of such a test object. It was possible to demonstrate in this way that with the tetrahedron point of design 1 having the arrangement described herein it is possible to reproduce for optical near-field microscopy a test object that can be recognized again, with a resolution of approximately 30 nm. Resolutions of 15 nm with the optical near field have been reported earlier; however, these did not involve structures that can be recognized again, so that it is not clear whether these structure details in fact represent a genuine reproduction of detail structures of the object.

(4) In connection with the special arrangement of the inverse photon tunnel microscope introduced here, the above-described arrangement is modified to the extent that the cover glass 7 is coated with an almost opaque metal layer of silver or gold, and that the object 6 is adsorbed on said metal layer. Light emitted by the near-field probe 1 does not penetrate into the collector through the metal film at spacings of the point from the object that are greater than one wavelength of the light. Only if the point is brought close to the object with spacings within the range of the wavelength, local surface plasmonas are stimulated within the zone of the point 2 and the oppositely disposed metal layer on the cover glass 7 when a suitable wavelength of the irradiation light is selected. Such surface plasmonas lead to stimulation of delocalized surface plasmonas in the metal layer, which in turn lead to reflection of light by the collector. In this way, a signal of the light transmitted by the collector is obtained that varies with the spacing, which signal is used for the inverse photon tunnel microscopy. Said arrangement has the property that the resonant plasmona stimulation is highly influenced by the refractive index of the object 6 in the gap between the point 2 and the metal layer (on support 7), and that for this reason it is possible to achieve a very high contrast of the near-field signal for slight variations of the refractive index of the object 6.

(5) Reflection arrangements.

Reflection arrangements for optical near-field microscopy expand the applicability of optical near-field microscopy to nontransparent objects (6). Two special reflection arrangements for optical near-field microscopy with the polyhedron point are explained in the following.

Figure 9:
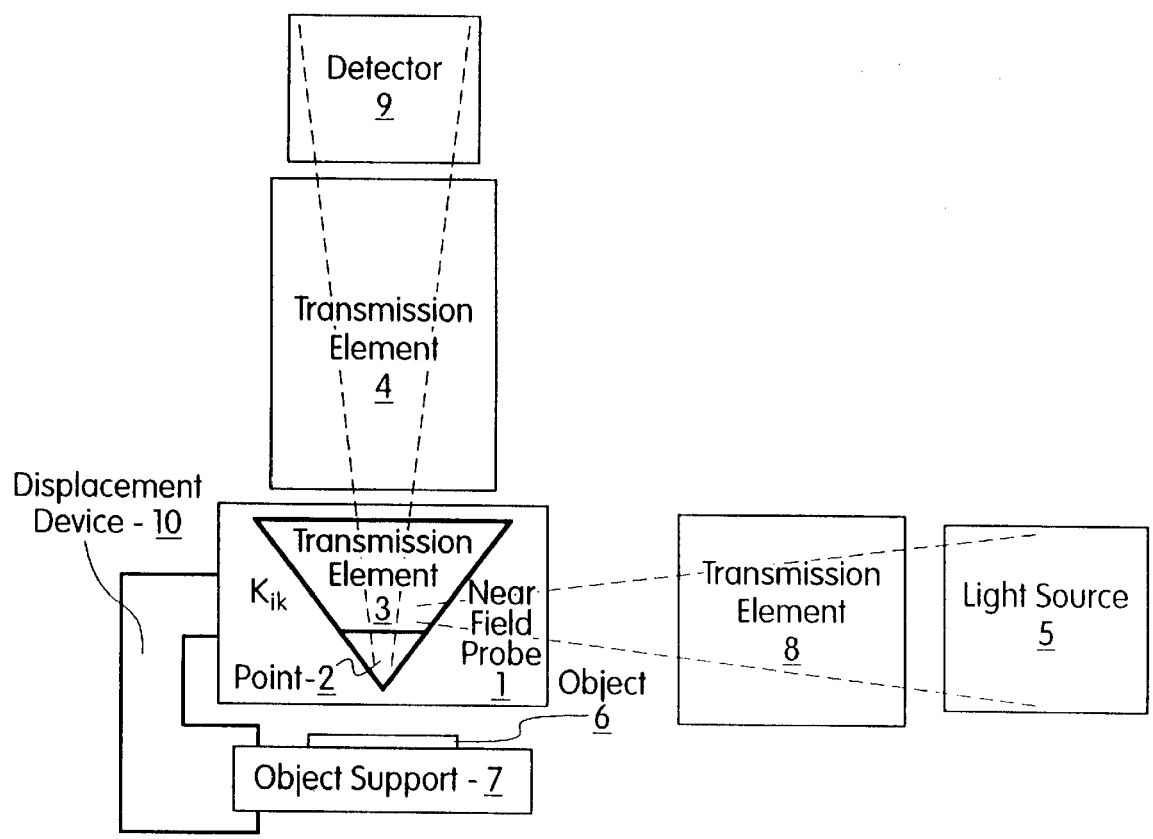
FIG. 9 shows a reflection arrangement with irradiation of the point from the outside.

(a) (FIG. 9) - The point 2 is irradiated from a light source 5 through a focusing transmission element 8, so that the beam of light is focused from the outside in the gap between the point 1 and the object 6 to a range of an edge $K_{ik}$ that reaches up to the point 2, or ends a few μm's from the latter. The light, which is reflected from the point into the polyhedron point and exits from the base surface $P_o$, is directed with the help of a microscope lens 4 at a detector 9 in the image plane of the lens, whereby the lens is adjusted in such a way that the point 2 is disposed in the plane of the lens.

Figure 10:
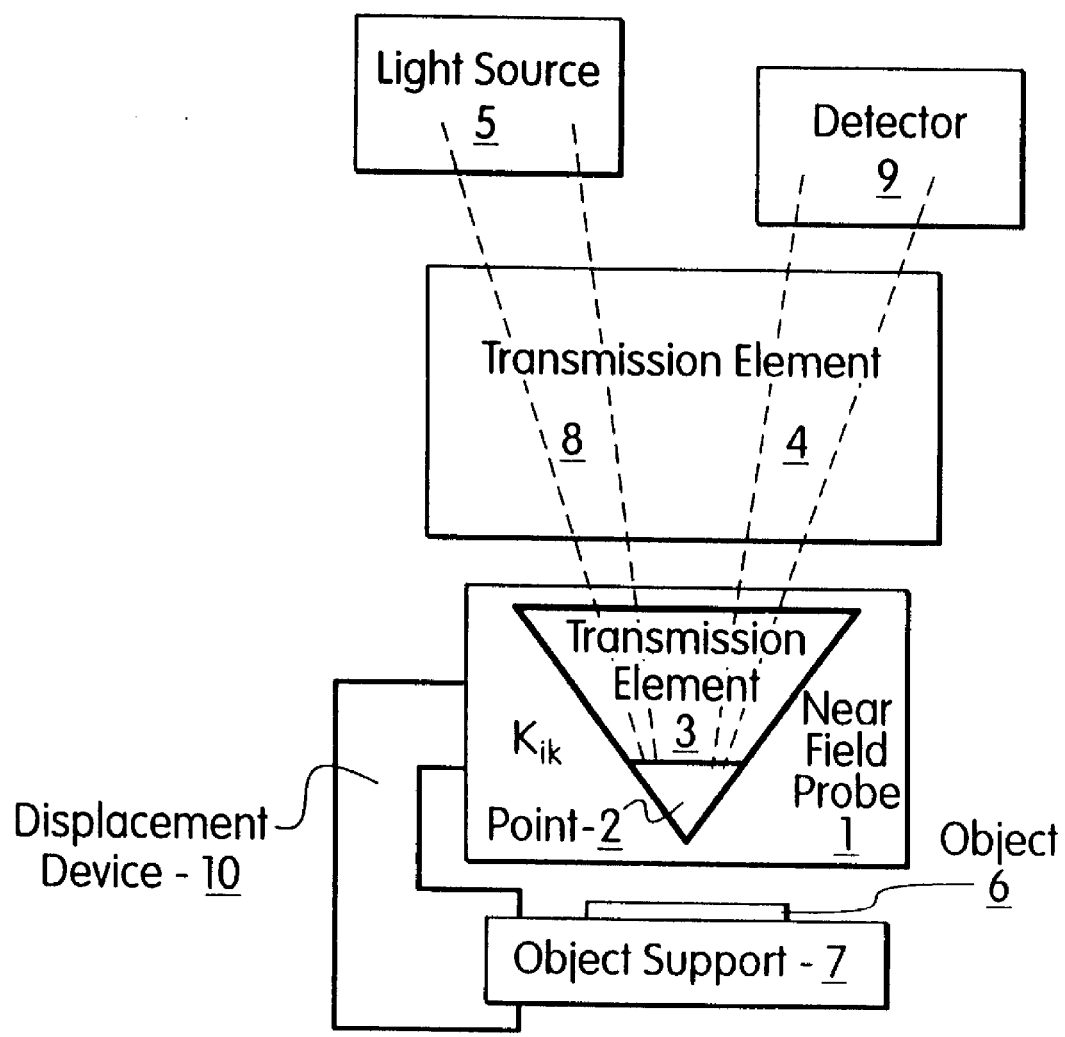
FIG. 10 shows a reflected-light type reflection arrangement.

(b) In a reflected-light reflection arrangement (FIG. 10), the polyhedron point 1 is irradiated from a light source 5 through a transmission element 4, 8, for example a microscope lens, in such a way that a focused beam is focused through the base surface $P_o$ on a zone of an edge $K_{ik}$ reaching up to the point 2 or ending a few μm's from the point. The light scattered back from the point 2 into the polyhedron point 3 and exiting through the base surface $P_o$ is directed at the detector with the help of the transmission element 4, 8.

(6) Arrangements for simultaneous SNOM and STM.

The near-field probe 1 is operated in any desired arrangement of optical near-field microscopy. A wire is contacted by way of an electrically conductive connection with the metal coating of the polyhedron point 1. Also, an electrically conductive site of the object is contacted with an electrical line. As commonly done in scanning tunnelling microscopy, a tunnel voltage is applied between the two electrical connections and the current is measured. Simultaneous; STM and SNOM can be realized in different ways. For example, in common STM, the current signal can be used for controlling the spacing between the point and the object. The follow-up signal is registered as the STM-signal for producing the picture. The optical signal is recorded as the signal for simultaneous optical near-field microscopy. Alternatively, the optical near-field signal can be used as described above for controlling the spacing, whereas the current signal is recorded as the STM-signal.

The arrangement 6 can be used also for testing light-induced influences on the tunnel current. Versus earlier arrangements for testing light-induced influences on the tunnel current (L. Arnold et al, Appl. Phys. Lett. 51, page 786; 1987), said arrangements offer the decisive advantage that irradiation of the object takes place only within a zone limited by the near-field probe, i.e., within a zone that is much Smaller than a zone irradiated through focusing.

The near-field probes can be used not only as probes for scanning near-field optical microscopy. They are generally usable as probes when measurement of local and also time-dependent optical properties is involved, such as measurement of the spatial distribution of electromagnetic radiation fields or near fields, measurement of time-dependent intensity variations in very small ranges, and measurement of the point transmission function of optical systems by arranging the emitting near-field probe in an inlet plane of the system as a point-like light source and measuring the intensity in another site as a function of the arrangement of the emitting probe.

I claim:

1. Microscopic transmitter or detector of electromagnetic radiation, which is near-field probe, comprising a body K having the form of a polyhedron point and comprising a material at least partially permeable to electromagnetic radiation in the spectral range used, whereby the polyhedron point is delimited by an imaginary base surface $P_o$ and continued beyond a substantial part of the body K to form a total body of the probe not defined in greater detail, and has "n" side surfaces $P_j$ (j=1, . . . , n), in a way such that sharp edges $K_{ik}$ are formed between adjacent side surfaces $P_j$ and $P_k$, such edges leading to an acute point;

said acute point of the near-field probe serves as an almost point-like source for the emission of electromagnetic radiation into the external space of the probe, or as an almost point-like receiver for the penetration of electromagnetic fields into the interior of the near-field probe;

at least two side surfaces $P_j$ (i=1, . . . , n) of the body K of the polyhedron probe are coated with thin electrically conductive layers partially absorbing the electromagnetic radiation in the special range used, said layers selected from the group consisting of aluminum, gold and silver and having a thickness of less than 0.2 μm; and the most frontal part of the polyhedron point is coated with the material used.

2. Near-field probe according to claim 1, wherein all side surfaces $P_i$ (i=1, ..., n) are coated with the coating material.

3. Near-field probe according to claim 1, wherein all edges $K_{ik}$ are coated with the coating material.

4. Near-field probe according to claim 1, wherein one edge $K_{i,k}$ between two adjacent coated sides $P_j$ and $P_k$ (i, k>0) is uncoated.

5. Near-field probe according to claim 1, wherein the body K of the polyhedron probe comprises photoluminescencing material, or that the material of the body is doped with photoluminescent centers in a zone of the surface including the point.

6. Near-field probe according to claim 1, wherein the body K of the polyhedron probe comprises nonlinear optical material with high nonlinear optical susceptibilities.

7. Device for optical near-field microscopy according to claim 1, comprising said near-field probe, and
a detector, and
a filter mounted upstream of the detector, and said filter suppressing the transmission of irradiation light.

8. Device for inverse photon tunnelling microscopy according to claim 1, comprising said near-field probe, and
an object support, and
a thin layer of silver or gold with a thickness of about 10 to 100 nm is a component of said object support, said layer being almost opaque to irradiation light and serving as a substrate for an object to be examined.

9. Device for optical near-field microscopy and simultaneous scanning tunnelling microscopy according to claim 1, comprising providing a near-field probe, and
an object, and
wherein coatings with coating material and said object are each provided with an electric contact, so that current flowing between the point and the object can be measured.

* * * * *